(12) United States Patent
KenKnight et al.

(10) Patent No.: US 6,251,125 B1
(45) Date of Patent: *Jun. 26, 2001

(54) METHOD AND APPARATUS FOR TREATING VENTRICULAR FIBRILLATION USING ELECTROGRAM FEATURES

(75) Inventors: Bruce H. KenKnight, Maple Grove; William Hsu, Circle Pines; Yayun Lin, St. Paul, all of MN (US); Janice Jones, Clarksburg, MD (US)

(73) Assignee: Cardiac Pacemakers, Inc., St. Paul, MN (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/053,115

(22) Filed: Apr. 1, 1998

Related U.S. Application Data

(63) Continuation of application No. 08/852,103, filed on May 6, 1997, now Pat. No. 6,112,117.

(51) Int. Cl.$^7$ .................................................. A61N 1/39
(52) U.S. Cl. .......................................................... 607/5
(58) Field of Search ................................................ 607/5, 4

(56) References Cited

U.S. PATENT DOCUMENTS

| | | | |
|---|---|---|---|
| Re. 35,779 | * 4/1998 | Alferness et al. | 607/5 |
| 4,202,340 | 5/1980 | Langer et al. | 128/419 |
| 4,787,389 | * 11/1988 | Tarjan . | |
| 4,940,054 | 7/1990 | Grevis et al. | 128/419 |
| 4,949,719 | 8/1990 | Pless et al. | 128/419 |
| 5,179,945 | 1/1993 | Hofwegen et al. | 128/419 |
| 5,179,946 | * 1/1993 | Weiss . | |
| 5,188,105 | 2/1993 | Keimel | 128/419 |
| 5,193,535 | * 3/1993 | Brady et al. | 607/5 |
| 5,301,677 | 4/1994 | Hsung | 128/705 |
| 5,325,856 | 7/1994 | Nitzsche et al. | 128/703 |
| 5,346,506 | * 9/1994 | Mower et al. | 607/7 |
| 5,350,406 | 9/1994 | Nitzsche et al. | 607/14 |

(List continued on next page.)

FOREIGN PATENT DOCUMENTS

| | | | |
|---|---|---|---|
| 0347708 | 12/1989 | (EP) | A61B/5/02 |
| 0550343 | 7/1993 | (EP) | A61N/1/38 |
| 0550344 | 7/1993 | (EP) | A61N/1/39 |
| 0674916 | 10/1995 | (EP) . | |
| 93/20888 | 10/1993 | (WO) | A61N/1/365 |
| 96/32984 | 10/1996 | (WO) . | |
| 97/06854 | 2/1997 | (WO) . | |

OTHER PUBLICATIONS

Hsia, P.W., et al., "Absolute Depolarization Vector Characteristics Associated with Successful Defibrillation: Evidence of a Vulnerable Period During Ventricular Fibrillation", *Supplement III Circulation*, vol. 82, No. 4, III–738, (Oct. 1990).

(List continued on next page.)

*Primary Examiner*—William E. Kamm
*Assistant Examiner*—Carl H. Layno
(74) *Attorney, Agent, or Firm*—Schwegman, Lundberg, Woessner & Kluth, P.A.

(57) ABSTRACT

A method and system for ventricular defibrillation by coordinating the delivery of defibrillation shocks with sensed ventricular fibrillation complexes in a way which improves the probability of success of the defibrillation shock. Ventricular electrical activity is monitored in two ventricular locations during ventricular fibrillation to detect coarse ventricular fibrillation complexes and contractions of the ventricular cardiac tissue. The defibrillation shock is delivered in coordination with the occurrence of coarse ventricular fibrillation complexes and the contractions of ventricular cardiac tissue, and specifically to occur on the up-slope portion thereof, for optimal probability of success.

22 Claims, 11 Drawing Sheets

U.S. PATENT DOCUMENTS

| | | | |
|---|---|---|---|
| 5,439,453 | | 8/1995 | Duong-Van ............................... 607/5 |
| 5,489,293 | | 2/1996 | Pless et al. .............................. 607/5 |
| 5,500,008 | | 3/1996 | Fain ........................................ 607/5 |
| 5,522,853 | | 6/1996 | Kroll ...................................... 607/5 |
| 5,540,723 | | 7/1996 | Ideker et al. ............................ 607/7 |
| 5,545,205 | | 8/1996 | Schulte et al ........................ 607/123 |
| 5,632,766 | * | 5/1997 | Hsu et al. ............................... 607/5 |
| 5,709,215 | | 1/1998 | Perttu et al. . |
| 5,797,967 | * | 8/1998 | KenKnight . |
| 5,978,704 | * | 11/1999 | Ideker et al. ............................ 607/5 |
| 5,978,705 | * | 11/1999 | KenKnight et al. ..................... 607/5 |

OTHER PUBLICATIONS

Hsia, P.W., et al., "Genesis of SIgmoidal Dose–Response Curve During Defibrillation by Random Shock: A Theoretical Model Based on Experimental Evidence for a Vulnerable Window During Ventricular Fibrillation", *Pace*, vol. 13, 1326–1342, (Oct. 1990).

Hsia, P.W., et al., "Improved Nonthoractomy Defibrillation Based on Ventricular Fibrillation Waveform Characteristics", *PACE*, 18, 803, Abstract No. 29, (Apr. 1995, Part II).

Hsu, W., et al., "Effect of Shock Timing on Defibrillation Success", *Pace*, 20 (part II), 153–157, (1997).

Jones, D.L., et al., "Ventricular Fibrillation: The Importance of Being Coarse?", *J. Electrocardiology*, 17, No. 4, 393–400 (1984).

Kuelz, K.W., et al., "Integration of Absolute Ventricular Fibrillation Voltage Correlates with Successful Defibrillation", *IEEE Transactions on Biomedical Engineering*, 41, No. 8, 782–791, (Aug. 1994).

Mower, M.M., et al., "Synchronization of Low–Energy Pulses to Rapid Deflection Signals as a Possible Mechanism of Subthreshold Ventricular Defibrillation", *Abstracts of the 55th Scientific Sessions*, II–75, Abstract No. 298, (1982).

* cited by examiner

METHOD AND APPARATUS FOR TREATING VENTRICULAR FIBRILLATION USING ELECTROGRAM FEATURES

CROSS REFERENCE TO RELATED APPLICATION

This application is a continuation of application Ser. No. 08/852,103, filed May 6, 1997, now U.S. Pat. No. 6,112,117 which is incorporated herein by reference.

FIELD OF THE INVENTION

This invention pertains generally to implantable medical devices, and more particularly to implantable medical devices for applying coordinated defibrillation electrical energy to the heart.

BACKGROUND OF THE INVENTION

Electric shock defibrillation is a proven technique of treatment of the serious and immediately life-threatening condition of ventricular fibrillation. For patients known to be at risk, an implantable defibrillator may be used. Such devices contain an energy source, an electrode lead system in contact in the heart, a sensing system to detect the onset of fibrillation, and a pulse generator for delivering the defibrillation shock.

Existing devices are generally designed or programmed to deliver a shock or series of shocks at a fixed interval or intervals following the detection of the fibrillation, unless fibrillation spontaneously terminates on its own first, or until recovery is achieved, as evidenced by the resumption of normal ventricular rhythm. The amount of energy to be delivered in a shock must be carefully chosen. If too small, it may not be successful in terminating the fibrillation. On the other hand, the shock must not be so large that it causes damage to the myocardium. The device generally is designed in consideration of the limited energy storage in an implanted device.

Ventricular electrical signals may exhibit a pattern, known as "fine ventricular fibrillation" during ventricular fibrillation. The fine ventricular fibrillation is characterized by relatively low signal amplitude and lack of organized features. The ventricular electrical signals may also exhibit a pattern known as "coarse ventricular fibrillation," characterized by intervals of relatively higher amplitude, which may repeat, separated by fine ventricular fibrillation intervals. It has also been suspected that it is easier to defibrillate coarse ventricular fibrillation than fine ventricular fibrillation. Because of this, previous works have suggested the possibility of timing of defibrillation shocks to features of the ventricular fibrillation waveforms as a way to improve defibrillation efficacy. However, it has not been clear from such prior works, which features are important, and how to detect and coordinate to them. A need, therefore, exists in the art for a system that improves defibrillation therapy by using the minimal amount of energy necessary to bring about effective and efficient defibrillation.

SUMMARY OF THE INVENTION

The present invention provides an improved defibrillator system. The defibrillator system determines an optimal time for the delivery of defibrillation shocks, such that the shocks delivered have an improved probability of success in terminating the fibrillation. This improved efficacy provides important medical advantages to the patient, both in the greater probability of success of individual shocks, and also in the reduction in pulse energy and number of shocks needed to defibrillate. This in turn will result in a smaller implantable defibrillator that can deliver more shocks over the lifetime of the battery.

The defibrillator system detects characteristics of arrhythmia complexes which exist during ventricular fibrillation of a heart, and coordinates the delivery of ventricular defibrillation shocks with portions of the complexes. In one embodiment, the defibrillator system monitors a first cardiac signal across a first cardiac region. The first cardiac region, in one embodiment, is in a left ventricular cardiac region of the heart. Upon detecting a ventricular fibrillation of the heart, the defibrillator system delivers a defibrillation shock during, or at the termination, of a coupling interval time period. The coupling interval time period is a preprogrammed time which is started once a contraction of cardiac tissue is detected in the left ventricular cardiac region of the heart by the first cardiac signal. In one embodiment, the coupling interval time period is started once the contractions of cardiac tissue sensed in the first cardiac signal exceeds a predetermined threshold value.

In an additional embodiment for treating ventricular fibrillation, the defibrillator system monitors the first cardiac signal across the first cardiac region and a second cardiac signal across a second cardiac region. In one embodiment, the first cardiac region is a left ventricular cardiac region of the heart and the second cardiac region is a right ventricular cardiac region of the heart. Upon detecting a ventricular fibrillation, the defibrillator system delivers defibrillation shocks during the occurrence of both a coupling interval time period started once a contraction of cardiac tissue is detected in the left ventricular cardiac region of the heart and an up-slope portion of a coarse arrhythmia complex detected in the right ventricular cardiac region of the heart. Coarse ventricular fibrillation complexes are large amplitude cardiac electrogram signals detected during a ventricular fibrillation that display regular periodic electrogram wave structures.

In an additional embodiment, the defibrillator system counts the coarse ventricular fibrillation complexes detected in the second cardiac signal. Defibrillation shocks are then coordinated with the up-slope portion of an nth counted coarse ventricular fibrillation complex having an amplitude greater than a coarse complex threshold value. The coarse complex threshold value is based on a Standard Amplitude Morphology (SAM) value. A SAM value is an average ventricular contraction signal which is calculated from a predetermined number of the largest second cardiac signal peak-to-peak values detected over a predetermined time interval. In one embodiment the coarse complex threshold value is 50% of the calculated SAM value.

Additionally, the delivery of the defibrillation shock is coordinated with a coupling interval time period, which is started once a contraction of cardiac tissue sensed in the first cardiac signal exceeds the predetermined threshold value. Upon detecting such a signal, the defibrillator system starts a coupling interval timer which counts off the predetermined coupling interval time period. In one embodiment, the delivery of the defibrillation shock is coordinated to occur during the coupling interval time period for the first cardiac signal and the up-slope portion of the nth counted coarse ventricular fibrillation complex of the second signal having an amplitude greater than the coarse complex threshold value. In this way the defibrillation shock may be coordinated with a ventricular condition from the first cardiac signal and/or the up-slope portion of a ventricular fibrillation complex from the second cardiac signal.

DETAILED DESCRIPTION

In the following detailed description, reference is made to the accompanying drawings which form a part hereof and in which is shown by way of illustration specific embodiments in which the invention may be practiced. These embodiments are described in sufficient detail to enable those skilled in the art to practice and use the invention, and it is to be understood that other embodiments may be utilized and that electrical, logical, and structural changes may be made without departing from the spirit and scope of the present invention. The following detailed description is, therefore, not to be taken in a limiting sense and the scope of the present invention is defined by the appended claims and their equivalents.

One defibrillator system for treating ventricular fibrillation was provided in copending U.S. patent application Ser. No. 08/513,685, filed Aug. 11, 1995, which is hereby incorporated by reference in its entirety.

The embodiments of the present invention illustrated herein are described as being included in an implantable cardiac defibrillator, which includes pacing functions and modes known in the art. In an alternative embodiment, the present invention is implemented in an external defibrillator/monitor. Moreover, other embodiments exist which do not depart from the scope and spirit of the present invention.

Figure 1:
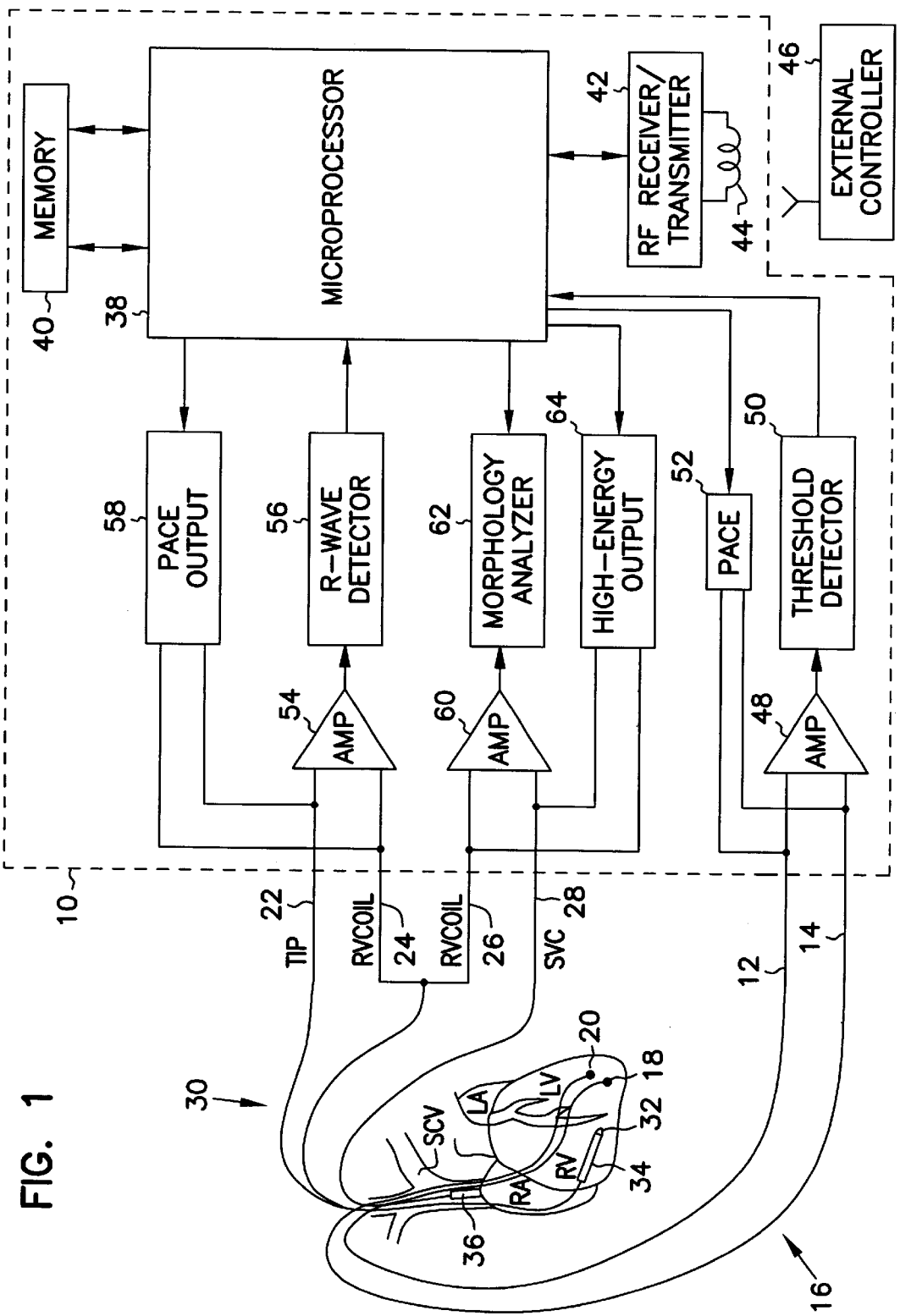
FIG. 1 is a block diagram of an embodiment of an implantable cardiac defibrillator of the type with which the defibrillator system may be implemented, including a diagrammatic representation of a first lead system and a second lead system placed in a heart.

In FIG. 1, an implantable cardiac defibrillator (ICD) 10 is shown in block diagram form. It includes terminals, labeled with reference numbers 12 and 14 for connection to a first lead system 16. The first lead system 16 is an endocardial lead, although other types of leads, such as epicardial leads, could also be used within the scope of the invention. The first lead system 16 is adapted for placement in a first cardiac region of the heart. In one embodiment, the first cardiac region of the heart is within the coronary sinus and/or the great cardiac vein of the heart adjacent to the left ventricle. The first lead system 16 includes a number of electrodes and electrical contacts. A tip electrode 18 is located at, or near, the distal end of the first lead system 16, and connects electrically to terminal 12 through a conductor provided within the first lead system 16. The first lead system 16 also includes a proximal electrode 20 which is spaced proximal the tip electrode 18. In one embodiment, the proximal electrode 20 is spaced proximal the tip electrode 18 for placement adjacent to the left ventricle of the heart. The proximal electrode 20 is electrically connected to terminal 14 through an internal conductor within the first lead system 16. The proximal electrode 20 can be of either an annular or a semi-annular construction, encircling or semi-encircling the peripheral surface of the first lead system 16.

The ICD 10 further includes terminals, labeled with reference numbers 22, 24, 26 and 28 for connection to a second lead system 30. The second lead system 30 is an endocardial lead. The second lead system 30 is adapted for placement within a second cardiac region of the heart. In one embodiment, the second cardiac region of the heart is the right ventricle of the heart. The second lead system 30 includes a number of electrodes and electrical contacts.

A tip electrode 32 is located at, or near, the distal end of the second lead system 30, and connects electrically through a conductor provided in the lead, for connection to terminal 22. The second lead system 30 further includes a first defibrillation coil electrode 34 spaced proximal to the distal end for placement in the right ventricle. The first defibrillation coil electrode 34 is electrically connected to both terminals 24 and 26 through internal conductors within the body of the second lead system 30. The second lead system 30 also includes a second defibrillation coil electrode 36, which is spaced apart and proximal from the distal end of the second lead system 30 such that the second defibrillation coil electrode 36 is positioned within the right atrium or major vein leading to the right atrium of the heart. The second defibrillation coil electrode 36 is electrically connected to terminal 28 through an internal conductor within the body of the second lead system 30.

The ICD 10 is a programmable microprocessor-based system, with a microprocessor 38 and memory 40, which contains parameters for various pacing and sensing modes. Pacing modes include, but are not limited to, normal pacing, overdrive or burst pacing, and pacing for prevention of ventricular tachyarrhythmias. Microprocessor 38 further includes means for communicating with an internal controller, in the form of an RF receiver/transmitter 42. This includes a wire loop antenna 44, whereby it may receive and transmit signals to and from an external controller 46. In this manner, programming commands or instructions can be transferred to the microprocessor 38 of the ICD 10 after implant. In one embodiment operating data is stored in memory 40 during operation. This data may be transferred to the external controller 46 for medical analysis.

The tip electrode 18 and the proximal electrode 20, connected through leads 12 and 14, serve to monitor a first cardiac signal across the first cardiac region. The tip electrode 18 and the proximal electrode 20, connected through leads 12 and 14, are applied to a sense amplifier 48, whose output is shown connected to a threshold level detector 50. These components also serve to sense and amplify signals indicative of the QRS waves of the heart, and apply the signals to the microprocessor 38.

In one embodiment, the microprocessor 38 responds to the threshold level detector 50 by providing pacing signals to a pace output circuit 52, as needed according to the programmed pacing mode. The pace output circuit 52 provides output pacing signals to terminals 12 and 14, which connects to the tip electrode 18 and the proximal electrode 20, for pacing. In one embodiment, pacing is provided in the range of 0.1–10 volts. In a further embodiment, filtering circuitry is incorporated into the circuitry of FIG. 1 to reduce signal noise from the first cardiac signal.

In the ICD 10, the tip electrode 32 and the first defibrillation coil electrode 34, connected through leads 22 and 24, are applied to a sense amplifier 54, whose output is connected to an R-wave detector 56. These components serve to amplify and sense the QRS waves of the heart, and apply signals indicative thereof to microprocessor 38. Among other things, microprocessor 38 responds to the R-wave detector 56, and provides pacing signals to a pace output circuit 58, as needed according to the programmed pacing mode. Pace output circuit 58 provides output pacing signals to terminals 22 and 24, which connect to the tip electrode 32 and the first defibrillation coil electrode 34, for the pacing modes as previously described.

In one embodiment, pacing pulses triggered by the pace output circuit 52 and the pace output circuit 58 are controlled by the microprocessor 38 to carry out a coordinated pacing scheme at the two ventricular pacing locations. Pacing modes include, but are not limited to, normal sinus rhythm pacing modes, overdrive or burst pacing modes for treating ventricular tachyarrhythmia, and/or pacing regimens for preventing the onset of a ventricular tachyarrhythmia. Additional advantages for providing pacing from the two ventricular pacing locations include the ability for either one of the two pacing systems to serve as a back-up pacing system and location for the other in the event that one pacing system were to fail.

The first defibrillation coil electrode 34 and the second defibrillation coil electrode 36 serve to monitor a second cardiac signal across the second cardiac region. The first and second defibrillation coil electrodes 34 and 36 are connected through leads 26 and 28 to a sense amplifier 60. The output of the sense amplifier 60 is connected to a morphology analyzer 62 that provides QRS morphology wave signals of the heart to the microprocessor 38. A high-energy output circuit 64 which operates under the control of the microprocessor 38, provides defibrillation level electrical energy to the patient's heart across the first defibrillation coil electrode 34 and the second defibrillation coil electrode 36. Alternatively, the high-energy output circuit 64 provides defibrillation level electrical energy to the patient's heart across either the first and second defibrillation coil electrodes, 34 and 36, and the housing of the defibrillator system, where the housing of the defibrillator system is configured as a "hot can" electrode.

Figure 2:
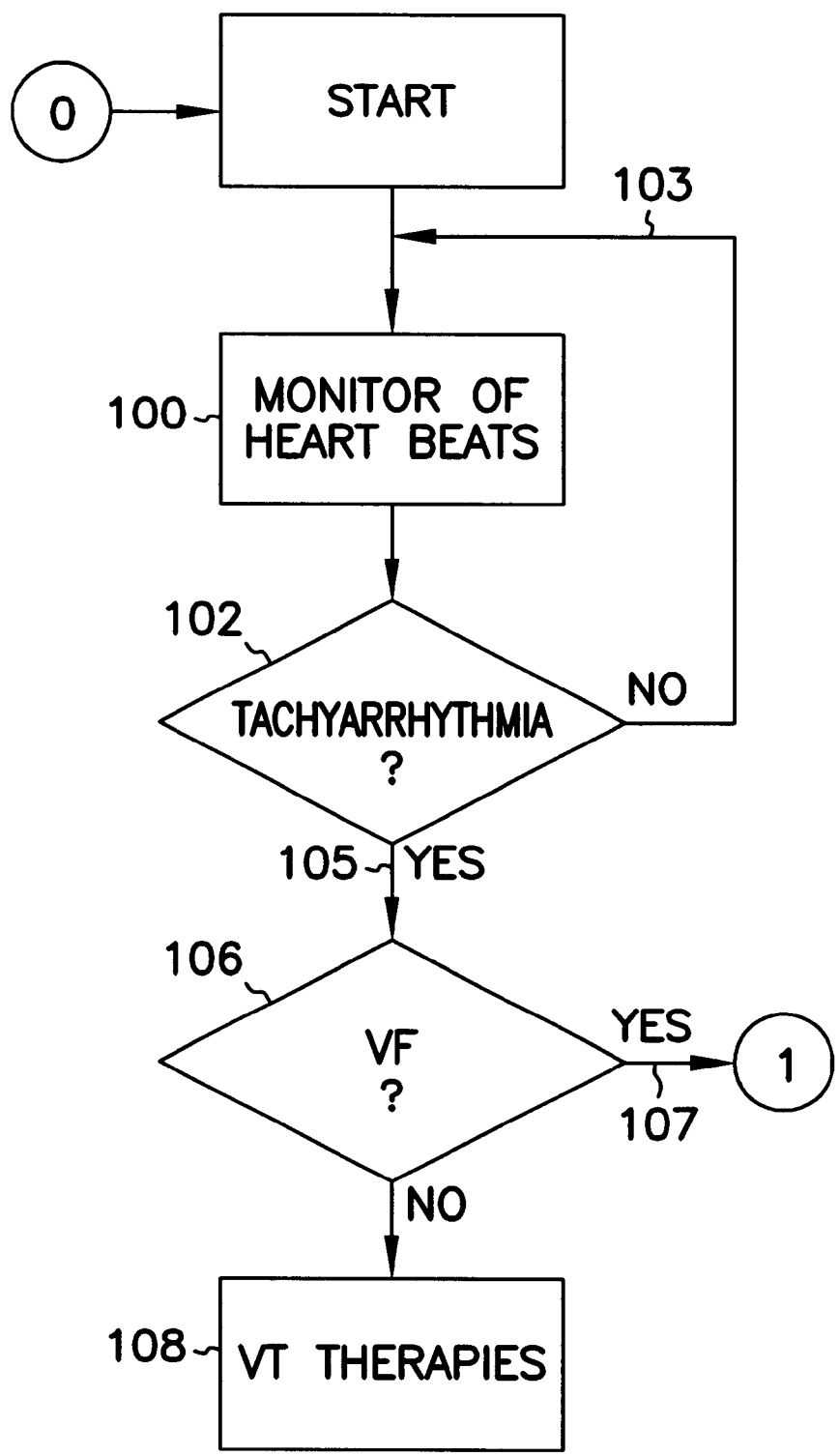
FIG. 2 is a flow chart illustrating a mode of operation of the implantable cardiac defibrillator of FIG. 1 in detecting tachyarrhythmia and ventricular fibrillation.

FIG. 2 illustrates overall modes of operation of the defibrillator system. In paced operation, the defibrillator system operates under programmed control to monitor heart beats occurring in the patient's heart. This is indicated by block 100 in FIG. 2. Such monitoring is accomplished through the sense amplifiers 48, 54 and 60, R-wave detectors 56, threshold level detector 50, and microprocessor 38 control in FIG. 1. Pacing may be administered as needed, depending upon the type of pacing functions provided in the ICD 10.

In one embodiment, the defibrillator system treats arrhythmias of a heart, such as ventricular fibrillations by initially monitoring the first cardiac signal across the first cardiac region, and the second cardiac signal across the second cardiac region. Decision block 102 tests whether a tachyarrhythmia has been detected. This is done through analysis of electrical signals from the heart under control of the microprocessor 38 and its stored program. In one embodiment, the decision block 102 uses a rate based determination to indicate the occurrence of a ventricular tachyarrhythmia. If such condition is not detected, control branches via path 103 back to the heart beat monitor block 100, and the process repeats.

If, however, a tachycardia arrhythmia condition is detected at decision block 102, control passes via path 105 to decision block 106, which tests for ventricular fibrillation, through analysis of heart signals as known in the art. In one embodiment, the determination of ventricular fibrillation is based on the rate of sensed ventricular contractions. If ventricular fibrillation is not detected, control branches to block 108 for ventricular tachyarrhythmia therapies. Ventricular tachyarrhythmia therapies can include, but are not limited to, the pacing therapies previously mentioned. If, however, at block 106, ventricular fibrillation is detected, control branches along path 107 to the ventricular fibrillation therapies of FIG. 5, FIGS. 7 and 8, or FIGS. 7 and 10 which include coordinated defibrillation shocks as described in greater detail below.

Figure 3:
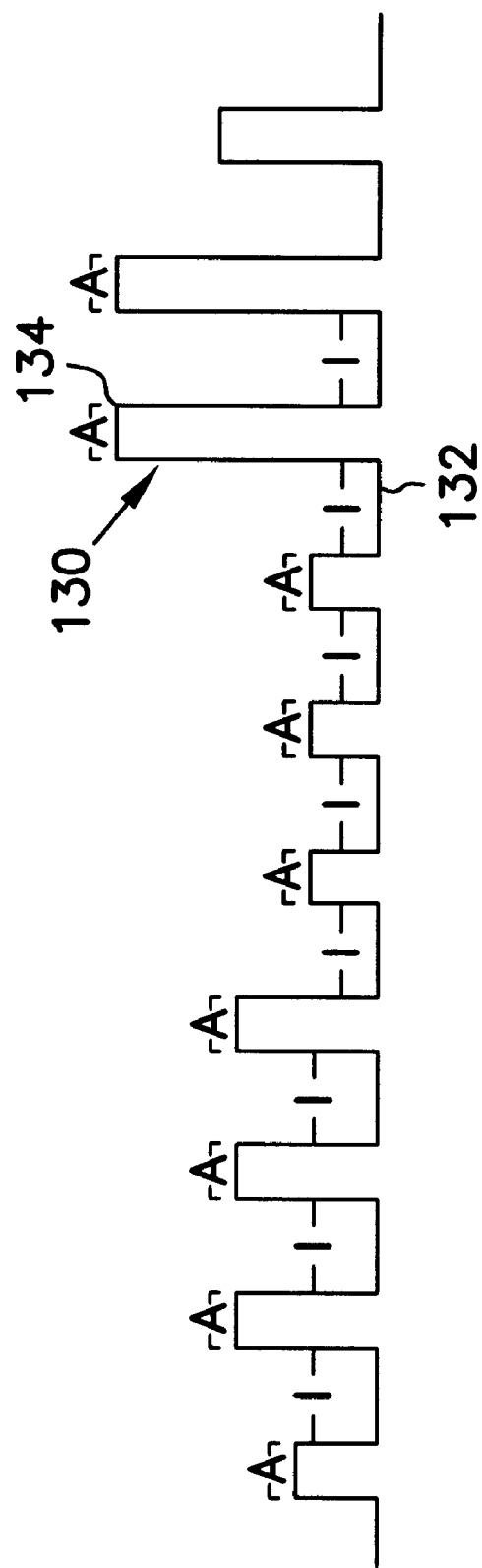
FIG. 3 is a waveform of a morphology signal from a heart in ventricular fibrillation.

FIG. 3 illustrates a first cardiac signal such as would be detected by the sensing amplifier 48, from a first cardiac signal appearing across the proximal electrode 20 and the tip electrode 18 on the first lead system 16. For other types of lead systems, similar or corresponding signals would be present. In FIG. 3, the wave form is an example of a voltage signal at the sense amplifier 48. The vertical axis represents amplitude, and the horizontal axis represents time. The zones designated as "A" represent active ventricular cardiac tissue in the region of the tip electrode 18 and the proximal electrode 20. Zones designated as "I" represent inactive ventricular cardiac tissue in the region of the tip electrode 18 and the proximal electrode 20. Within an "A" complex, a single peak feature of the complex is indicated by reference number 130. The difference in amplitude between the amplitude extremes, 132, 134, indicates the peak-to-peak amplitude calculation which is used as a part of the method of the invention.

Figure 4:
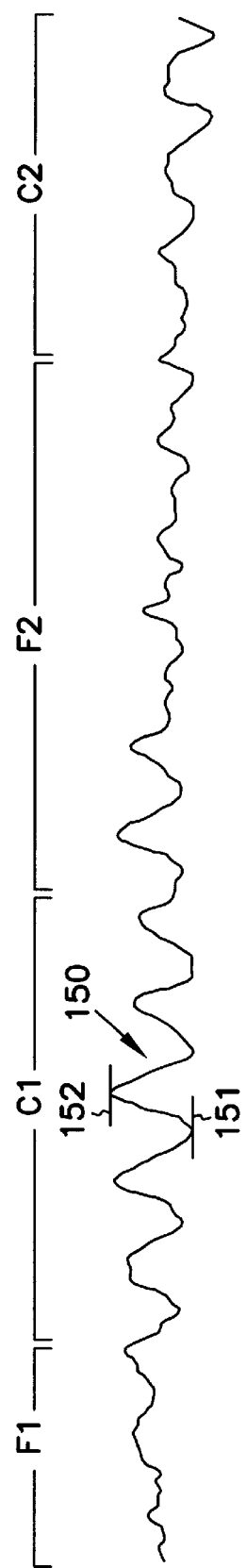
FIG. 4 is a waveform of a signal from a heart in ventricular fibrillation.

FIG. 4 illustrates an electrogram morphology signal from cardiac ventricular activity. This second cardiac signal is monitored across the second cardiac region. In one embodiment, the second cardiac signal is monitored between the first defibrillation coil electrode 34 and the second defibrillation coil electrode 36 on the second lead system 30. For other types of lead systems, similar or corresponding signals are present. In FIG. 4, the wave form is an example of a voltage signal at the sense amp 60. The vertical axis represents amplitude, and the horizontal axis represents time. As used herein, the heart (morphology) signals are represented as what is considered as normal polarity of signals from the heart. Thus, references to increasing signal, positive slope, or up-slope, are all with reference to normal polarity. Reversing the polarity of the leads would cause reversal of the polarity of the signal, in which case a corresponding reversal of positive slope to negative slope. If the polarity of sensing is changed, the defibrillator system coordinates defibrillation shocks on negative-going signals. In one embodiment, the absolute value of the sensed signal could be used, which would correspond to either positive or negative polarity signals. For purposes of the remainder of this detailed description, positive or normal polarity will be assumed.

In FIG. 4, Zones F1 and F2 show regions of fine ventricular fibrillation. Zones C1 and C2 show coarse ventricular fibrillation complexes. Coarse ventricular fibrillation complexes are large amplitude cardiac electrogram signals detected during a ventricular fibrillation that display regular periodic electrogram wave structures. Within complex C1, a single peak feature of the complex is indicated by reference number 150. The difference in amplitude between the amplitude extremes, 151, 152, indicates the peak-to-peak amplitude. The peak-to-peak amplitude values are used in the calculation of a Standard Amplitude Morphology (SAM) value. In one embodiment, the SAM value is calculated by averaging a predetermined number of the largest peak-to-peak values detected over a predetermined time interval. The predetermined time interval can be programmed within a range of 1–10 seconds. Also, the predetermined number of the largest peak-to-peak values can be programmed within a range of 3–10. The coarse complex threshold value is then based on the calculated SAM value, where in one embodiment the coarse complex threshold value is 50% of the SAM value.

Figure 5:
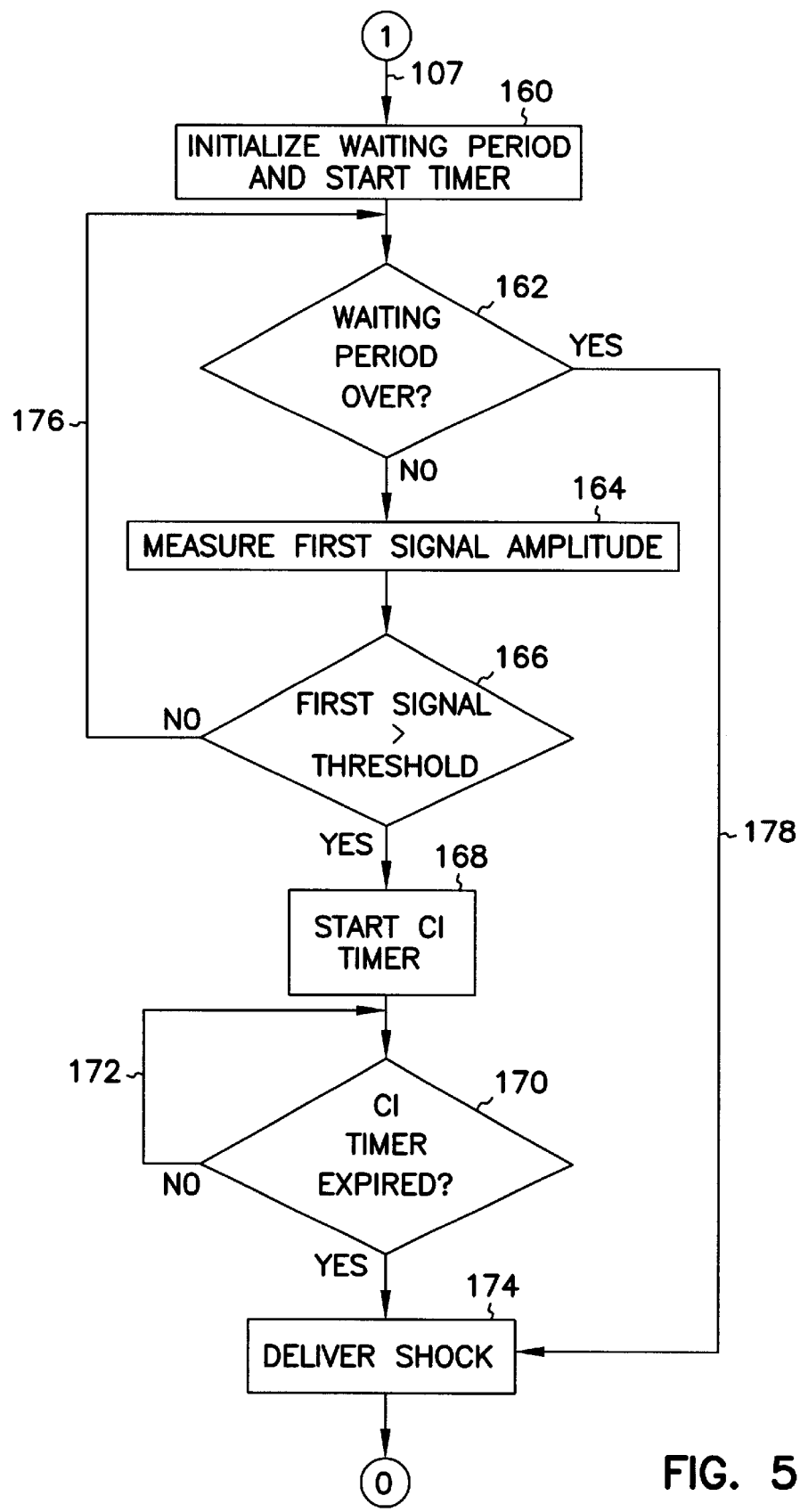
FIG. 5 is a flow chart illustrating one embodiment of the operation of the defibrillator system of FIG. 1 for delivering defibrillation shocks coordinated with ventricular fibrillation features.
Figure 6:
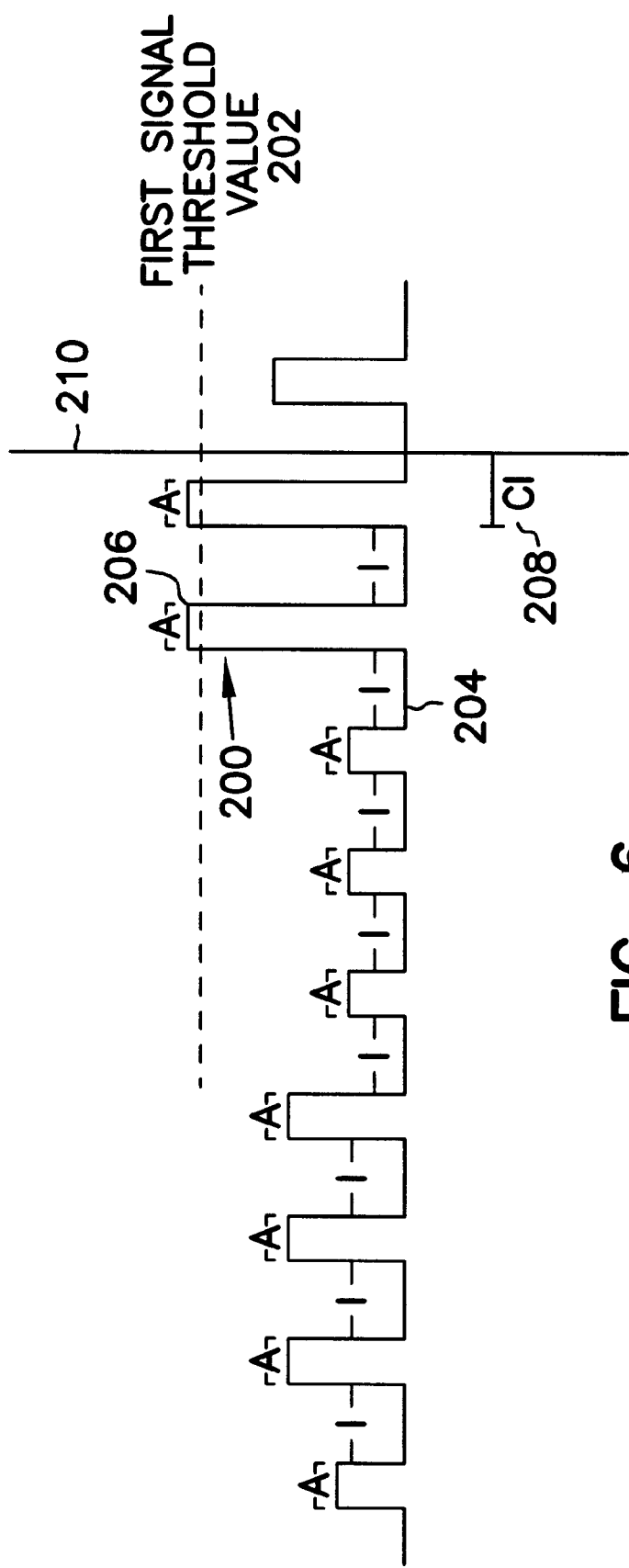
FIG. 6 is a waveform of a first signal from a heart in ventricular fibrillation, and illustrating the delivery of the defibrillation shock coordinated with ventricular fibrillation features of the first signal.

Referring now to FIGS. 5 and 6, there is shown one embodiment of the method of treating ventricular fibrillation using the defibrillation system for delivering coordinated defibrillation shocks based on ventricular activity signals from the first cardiac signals. In one embodiment, the defibrillation system monitors the first cardiac signal across a left ventricular cardiac region of the heart. Path 107 is continued from FIG. 2.

At step 160, a waiting period is initialized, and a waiting period timer is started. The waiting period timer defines the time period during which coordinated defibrillation shocks may be attempted, and after which the defibrillator system will deliver asynchronous defibrillation shocks. This time period is programmable as one of the programming parameters for the ICD 10 microprocessor 38. This time period must be kept within reasonable physiological limits, before going to asynchronous mode. In one embodiment, the waiting period timer is programmed within the range of 10–40 seconds, where 10 seconds is an acceptable value.

Decision block 162, which potentially is looped through multiple times, tests whether the waiting period timer programmed for coordinated defibrillation shocks has passed. If not, control passes to step 164, where the amplitude of the first cardiac signal for a present or current point detected by the first lead system 16 is taken by sense amplifier 48. This could be done by hardware or software in the threshold level detector 50, part of which could also be done by software in microprocessor 38.

According to one embodiment of the present invention, at step 166 the defibrillator system tests whether the amplitude of the first cardiac signal 200 has exceeded a predetermined threshold value 202. Determining if the a first cardiac signal 200 has exceeded the predetermined threshold value 202 is accomplished by comparing the amplitude of the current point of the first cardiac signal 200 to the predetermined threshold value 202 programmed into memory 38. The amplitude of the current point of the first cardiac signal 200 is calculated by taking the difference in amplitude between the signal amplitude extremes 204 and 206 of the first signal. The predetermined threshold value 202 can be programmed in the ranges of 0.1–10 millivolts.

At step 166, if the value of the measured first cardiac signal exceeds the predetermined threshold value 202, the defibrillator system starts a coupling interval timer at step 168. The coupling interval timer times out a coupling interval time period 208, during which a coordinated defibrillation shock 210 can be delivered. Alternatively, the coordinated defibrillation shock 210 is delivered at the expiration of the coupling interval time period 208. The coupling interval period is a programmable value in the range of 0–200 milliseconds, where 0–30 milliseconds is an acceptable range of values.

At step 170, the defibrillator system tests whether the CI timer has expired. If the CI timer has not expired, control passes via 172 to loop through step 170 again. After the CI timer has expired, control passes to step 174, which causes the high-energy output circuit 64 to deliver the defibrillation shock 210.

Alternatively, while the defibrillator system is monitoring the heart, if the waiting period for the defibrillator system times out without finding the required conditions for coordinated defibrillation shocking (i.e, the first cardiac signal does not exceed the predetermined threshold value 202), then once the defibrillator system loops back to 162 along path 178 control passes via path 178 to step 174 where the defibrillator system proceeds to deliver an asynchronous defibrillation shock.

Following the delivery of the defibrillation shock, the sensing circuits of the ICD check to see whether the shock was successful, that is, whether the ventricular fibrillation has stopped. This is represented by a return to point "0" at the start of FIG. 2. If not successful, and if ventricular fibrillation continues, this is detected in FIG. 2, and control passes again to FIG. 5 to repeat the ventricular fibrillation therapy. In one embodiment, the waiting period (step 162) for the second or higher passes is by-passed. In one embodiment, the waiting period (step 162) for the second or higher passes is separately programmed from the first pass. Then if the first shock fails, the process of sensing and coordination for delivery for a second shock can begin immediately.

Figure 7:
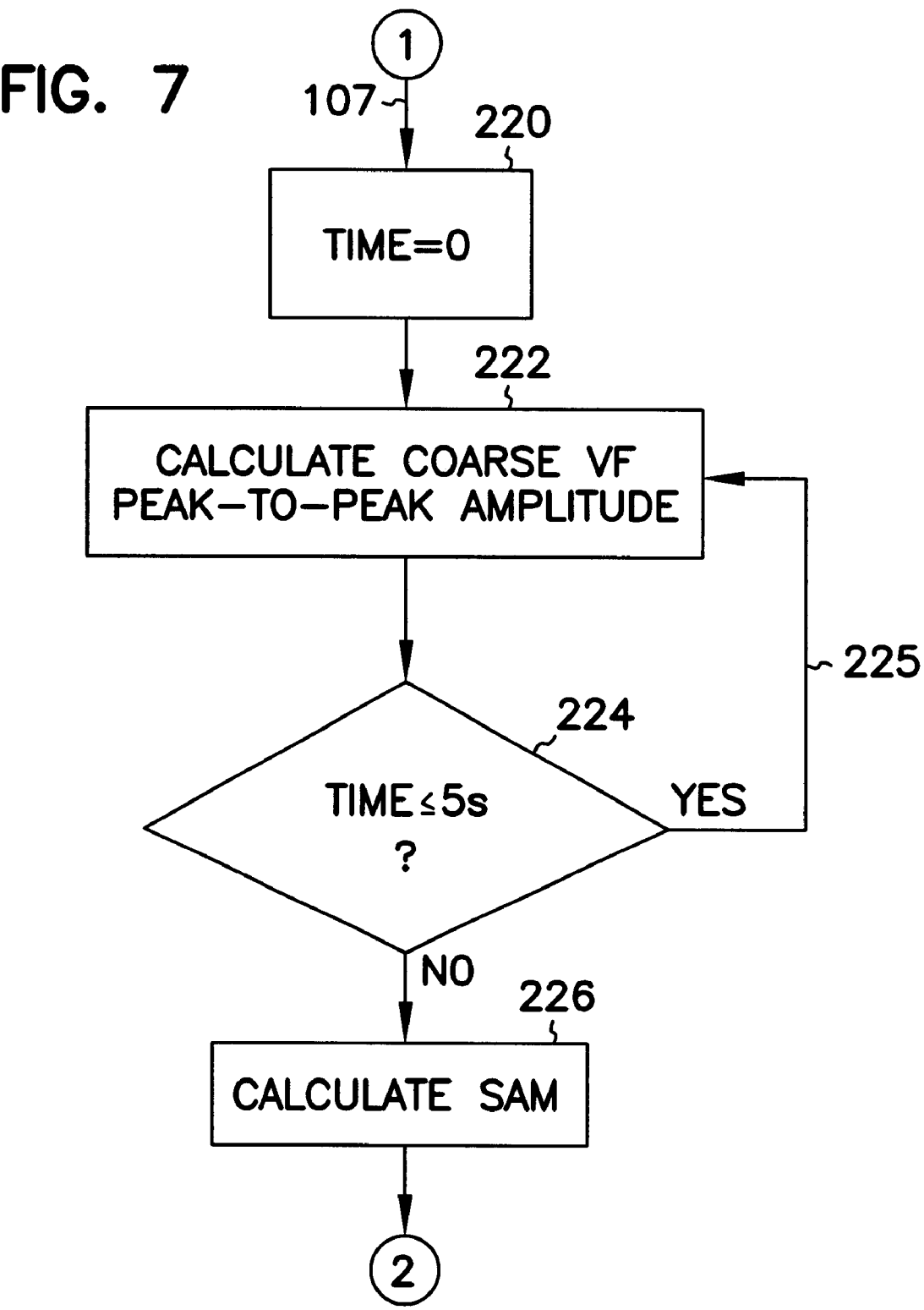
FIG. 7 is a flow chart illustrating the computation of Standard Amplitude of Morphology (SAM) by the defibrillator system.

In an alternative embodiment, both the first and the second cardiac signals are used in coordinating the delivery of a defibrillation shock to a heart experiencing ventricular fibrillation. In this embodiment, the defibrillation system monitors a second cardiac signal across a right ventricular region. In FIG. 7, path 107 is continued from FIG. 2. Upon occurrence or detection of a ventricular fibrillation condition, peak-to-peak amplitudes of coarse ventricular fibrillation complexes from the second cardiac signal are computed. In one embodiment, the peak-to-peak amplitudes of coarse ventricular fibrillation complexes are computed over a five second interval. The peak-to-peak amplitudes are from the second cardiac signals sensed by the sensing amp 60 across the first defibrillation coil electrode 34 and the second defibrillation coil electrode 36. The time duration of five seconds is a programmable value, and a different value may be used without departing from the scope of the invention.

At block 220, which is reached after a ventricular fibrillation has been detected in FIG. 2, a time is initialized at a starting or zero point. The coarse ventricular fibrillation amplitude value for the second cardiac signal are computed, based upon peak-to-peak value readings, as indicated in FIG. 4, at a computation block 222. This is accomplished by continually taking samples of the second ventricular morphology signals and comparing them with previously obtained samples. When such comparison shows a trend reversing, (i.e., from decreasing to increasing, or from increasing to decreasing in value) for the second cardiac signal a bottom or top (i.e., a peak, negative or positive) has been reached. Such peak values are then stored for each of the second ventricular morphology signals for comparison with other peak values as part of the SAM calculation. For each peak occurring in a coarse ventricular fibrillation complex, the high and low values, and hence the peak-to-peak values, are calculated and stored for the second cardiac signals.

Flow then proceeds to decision block 224, where the time for the five-second interval is tested. If the five seconds (or other programmable interval) has not passed, flow branches back via path 225 to the computation block 222, and computation detection of peaks and computation of peak-to-peak value continues. If, however, the time has exceeded or equaled the five-second set interval, control passes to block 226. At block 226, the SAM value is calculated for the second cardiac signal, as being the average of the five largest peak-to-peak measurements during the five-second interval in FIG. 4. This is done through recall, comparison, and calculation based upon the stored peak values for the first cardiac signals.

Figure 8:
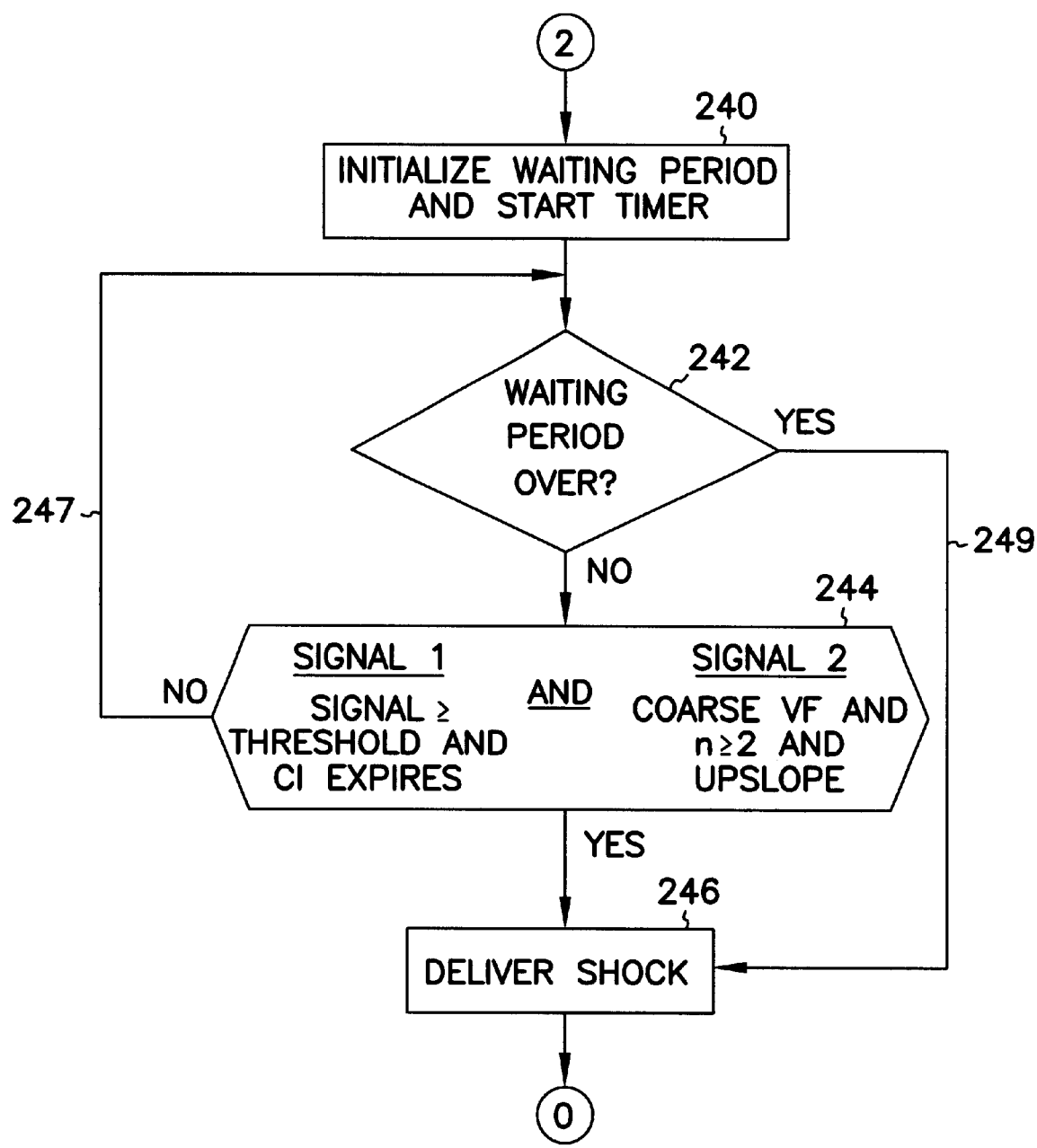
FIG. 8 is a flow chart illustrating one embodiment of the operation of the defibrillator system of FIG. 1 for delivering defibrillation shocks coordinated with ventricular fibrillation features.

FIG. 8 shows the operation of the defibrillator system for delivering coordinated defibrillation shocks based on ventricular activity signals from the first cardiac signals and on sensed coarse ventricular fibrillation complex features from the second cardiac signals. In one embodiment, the defibrillation shock is delivered to the heart during the occurrence of both a coupling interval time period started once a contraction of cardiac tissue is detected in the left ventricular cardiac region by the first cardiac signal and an up-slope portion of a coarse ventricular fibrillation complex as detected in the right ventricular cardiac region by the second cardiac signal.

The start of FIG. 8 is reached from the flow chart of FIG. 7. In the following embodiment, both the ventricular activity signals of the first cardiac signals and the sensed coarse ventricular fibrillation complex features of the second cardiac signals are taken into consideration in coordinating a defibrillation shock. At step 240, "n" (the count for a Candidate Morphology Complex discussed below) is set to zero, a waiting period is initialized, and a waiting period timer is started. The waiting period timer defines the time period during which coordinated defibrillation shocks may be attempted, and after which the defibrillator system will deliver asynchronous defibrillation shocks. This time period is programmable as one of the programming parameters for the ICD 10 microprocessor 38. This time period must be kept within reasonable physiological limits, before going to asynchronous mode. In one embodiment, the waiting period timer is programmed within the range of 10–40 seconds, where 10 seconds is an acceptable value.

Decision block 242, which potentially is looped through multiple times, tests whether the waiting period timer programmed for coordinated defibrillation shocks has passed. If not, control passes to step 244 where sensed conditions for the first cardiac signal and the second cardiac signal are assessed to determine if a coordinated defibrillation shock is to be delivered. In one embodiment, the conditions for the first cardiac signal and the second cardiac signal are concurrently analyzed at step 244 and both conditions must be satisfied in order for the defibrillator system to proceed to deliver a defibrillation shock to the heart at step 246.

In one embodiment, step 244 shows a list of conditions that must be detected in and satisfied for the first cardiac signal. In the present embodiment, the conditions monitored from the first cardiac signal include whether the first cardiac signal is greater than or equal to a predetermined threshold value and whether a coupling interval timer has expired.

The amplitude of the first cardiac signal for a present or current point detected by the first lead system 16 is taken by sense amplifier 48. This could be done by hardware or software in the threshold level detector 50, part of which could also be done by software in microprocessor 38. According to one embodiment of the present invention, at step 244 the defibrillator system concurrently tests whether the first cardiac signal has exceeded the predetermined threshold during an episode of coarse ventricular fibrillation detected in the first cardiac signal.

In one embodiment, determining if the a first cardiac signal has exceeded the predetermined threshold is accomplished by comparing the amplitude of the current point of the first cardiac signal to a predetermined amplitude value programmed into memory 40. The predetermined threshold value can be programmed in the ranges of 0.1–10 millivolts.

Once a first cardiac signal exceeds the predetermined threshold the defibrillator system starts the coupling interval timer. The coupling interval timer times out a coupling interval time period, over which a coordinated defibrillation shock can be delivered. The coupling interval time period is programmed in the range of 0–200 milliseconds, where 0–30 milliseconds is an acceptable range of values.

Step 244 also shows a list of conditions that must be detected in and satisfied for the second cardiac signal. In the present embodiment, the conditions monitored from the second cardiac signal include whether the second cardiac signal is a coarse ventricular fibrillation, with a coarse morphology complex value equal to or greater than a predetermined value and is on an upslope portion of the coarse ventricular fibrillation complex. Other combinations of sensed characteristics from the second cardiac signals, however, could be used for coordinating the delivery of a defibrillation shock with the first cardiac signal.

The amplitude of the morphology of the second cardiac signal detected by the second lead system 30 is taken by sense amp 60. This could be done by hardware or software in the morphology analyzer 62, part of which could also be done by software in microprocessor 38.

In one embodiment, the defibrillator system counts the occurrences of coarse ventricular fibrillation complexes detected in the second cardiac signal. For the second cardiac signal, the amplitude of the current point is compared to a coarse complex threshold value. If the second cardiac signal of the current point has a peak-to-peak amplitude greater than or equal to the coarse complex threshold value, then the current point is identified as a Candidate Morphology Complex (CMC) for the second cardiac signal, and a count "n" of a second signal CMC is incremented by one. In one embodiment of the present invention, the coarse complex threshold value is 50% of the calculated SAM value.

In an additional embodiment, the value for "n" CMC is a programmable number greater than or equal to 2 and less than or equal to about 9. In the embodiment shown in FIG. 8, the "n" for the CMC is programmed to 2. At step 146, once the "n" CMC count value is equal to or above programmed number, the defibrillator system assess the slope of the second cardiac signal to determine if the coarse ventricular complex signal is on an upslope portion of the signal. In one embodiment, the defibrillator system test whether the current point for the second cardiac signal is on an up-slope, i.e. having a positive slope by comparing the amplitude of the current point of the second signal to the amplitude of the previous second signal point, to determine the trend.

In one embodiment, if any of the conditions for either the first cardiac signal or the second cardiac signal are not satisfied, control branches to path 247, to repeat the loop. If, however, these conditions are met for both the first cardiac signal and the second cardiac signal, control passes to step 246 where the defibrillator system proceeds to deliver a defibrillation shock. Also, if during this testing process the waiting period for the defibrillator system times out without finding the required conditions for coordinated defibrillation shocking, then once the defibrillator system loops back to 242 control passes via path 249 to step 246 where the defibrillator system proceeds to deliver an asynchronous defibrillation shock.

Figure 9:
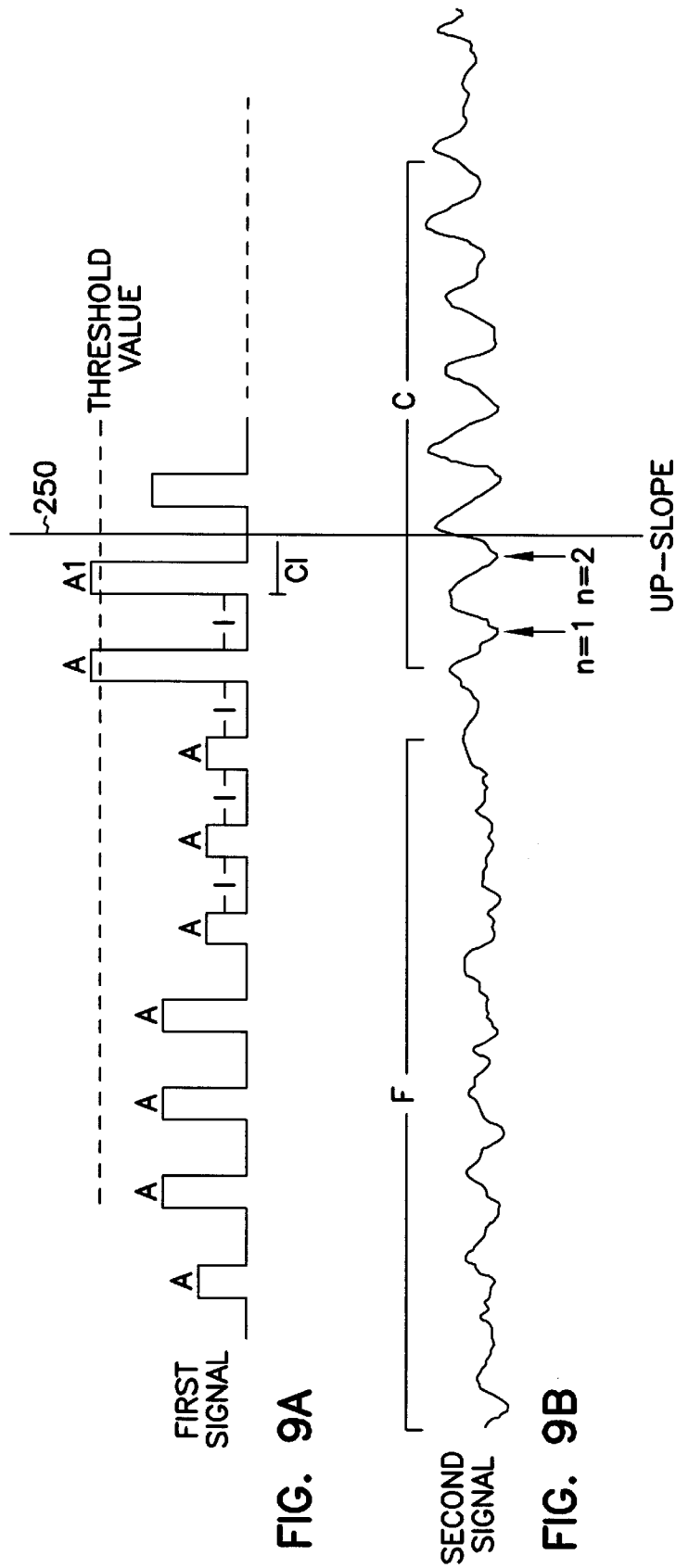
FIGS. 9A and 9B are waveforms of a first and a second signal from a heart in ventricular fibrillation, and illustrating the delivery of the defibrillation shock coordinated with ventricular fibrillation features of the first and second signals.

FIG. 9 shows an example of the waveforms of the defibrillator system used for delivering coordinated defibrillation shocks based on sensed coarse ventricular fibrillation complex features from the first cardiac signals and from the second cardiac signals. In FIG. 9A, for the first cardiac signal, the zones labeled "A" are areas of active ventricular tissue and the zones labeled "I" are area of inactive ventricular tissue. In FIG. 9B, for the second cardiac signal, the zones labeled "F" are areas of fine ventricular fibrillation, and the zones labeled "C" are areas of coarse ventricular fibrillation complexes. As the ventricular fibrillation is occurring in real time, the defibrillator system is sensing and monitoring the first cardiac signal at the first cardiac region and the morphology of the second cardiac signal at the second cardiac region. For the second cardiac signal, after the first major peak indicated, the defibrillator system has determined that a peak of a possible coarse ventricular fibrillation complex for the second cardiac signal has occurred, and the CMC count is incremented at the peak "n=1". Assume, as is the case in FIG. 9, that it is in fact the start of a ventricular fibrillation complex. The second peak "n=2" is counted as 2.

The defibrillator system senses and analyzes the first cardiac signal as it is sensing and analyzing the second cardiac signal. For the first cardiac signal, after the first active area A1 for the first cardiac signal has exceeded the predetermined threshold during an episode of coarse ventricular fibrillation, the CI timer is started. On the next up-slope of the second cardiac signal, as the amplitude of an up-slope signal passes the coarse complex threshold value (in the present embodiment this value is 50% of the calculated SAM value), on a first signal CMC peak count of n=2 or more and with the CI timer not having been exceeded the decision is made based on these criteria to deliver the defibrillation shock. The microprocessor 38 and high-energy output circuit 64 then deliver the shock shortly thereafter based on this decision. The defibrillation shock is indicated at line 250.

Following the delivery of the defibrillation shock, the sensing circuits of the ICD check to see whether the shock was successful, that is, whether the ventricular fibrillation has stopped. This is represented by a return to point "0" at the start of FIG. 2. If not successful, and if ventricular fibrillation continues, this is detected in FIG. 2, and control passes again to FIG. 8 to repeat the ventricular fibrillation therapy. The waiting period (steps 240, 242) for the second or higher passes can preferably be by-passed (or at least separately programmed from the first pass). Then if the first shock fails, the process of sensing and coordination for delivery for a second shock can begin immediately.

In an alternative embodiment, the defibrillator system and method of delivering coordinated defibrillation shocks of the present invention is based either on coarse ventricular fibrillation complex features on left ventricular conditions from the first cardiac signal or from the second signal. In this situation, the ventricular fibrillation complex characteristics detected by the first signal and the second signal are logically "OR"ed together in the determination to provide defibrillation shocks. Therefore, if during an episode of ventricular fibrillation the defibrillator system does not satisfy the left ventricular electrogram condition (e.g., the amplitude of the first signal does not exceed a predetermined threshold value) and the right ventricular electrogram signals are coarse, the defibrillator system will deliver coordinated defibrillation shocks based on the sensed coarse ventricular fibrillation complex features as previously described. Likewise, when the left ventricular electrogram condition of the first signal become satisfied, but the right ventricular electrogram signal of the second signal does not detect the occurrence of coarse ventricular fibrillation complexes, the defibrillator system can deliver a defibrillation shock at or before the expiration of the CI timer.

In a further embodiment, additional sensing and/or defibrillation electrodes are placed in contact with the patient (e.g., subcutaneous, epicardial, and/or endocardial electrodes) and electrically coupled to the ICD 10. The additional sensing and/or defibrillation electrodes are used in sensing cardiac morphology signals from the left ventricle between the electrodes on the first lead system 20 and the additional sensing and/or defibrillation electrodes. The morphology signals from the first lead system 16 located in the left ventricular region are processed as the morphology signals from the second lead system 30, where the nth counted coarse ventricular fibrillation in the second signal (i.e., the CMC count) further includes an mth counted coarse ventricular fibrillation in the first signal. The mth counted coarse ventricular fibrillation is a programmable number which is greater than or equal to 2 and less than or equal to 9.

The first and second morphology signals are then used to base the delivery of defibrillation shocks to a heart experiencing ventricular fibrillation. For example, during a detected ventricular fibrillation episode SAM values (first and second predetermined values for the first and second signals) and CMC values (mth and nth values for the first and second signals) are calculated for both the first and the second cardiac signals and utilized by the defibrillator system to base the delivery of a defibrillation shock. It is, therefore, possible to coordinate defibrillation shocks to be delivered when, for example, both ventricular morphology signals indicating a coarse ventricular fibrillation complex have satisfied their CMC value requirements and both coarse ventricular fibrillation signals are on an up-slope portion of their respective signals. Alternatively, one signal's up-slope portion could be programmed to be a dominate signal and the defibrillation shock would be delivered regardless of the slope of the other morphology signal.

Figure 10:
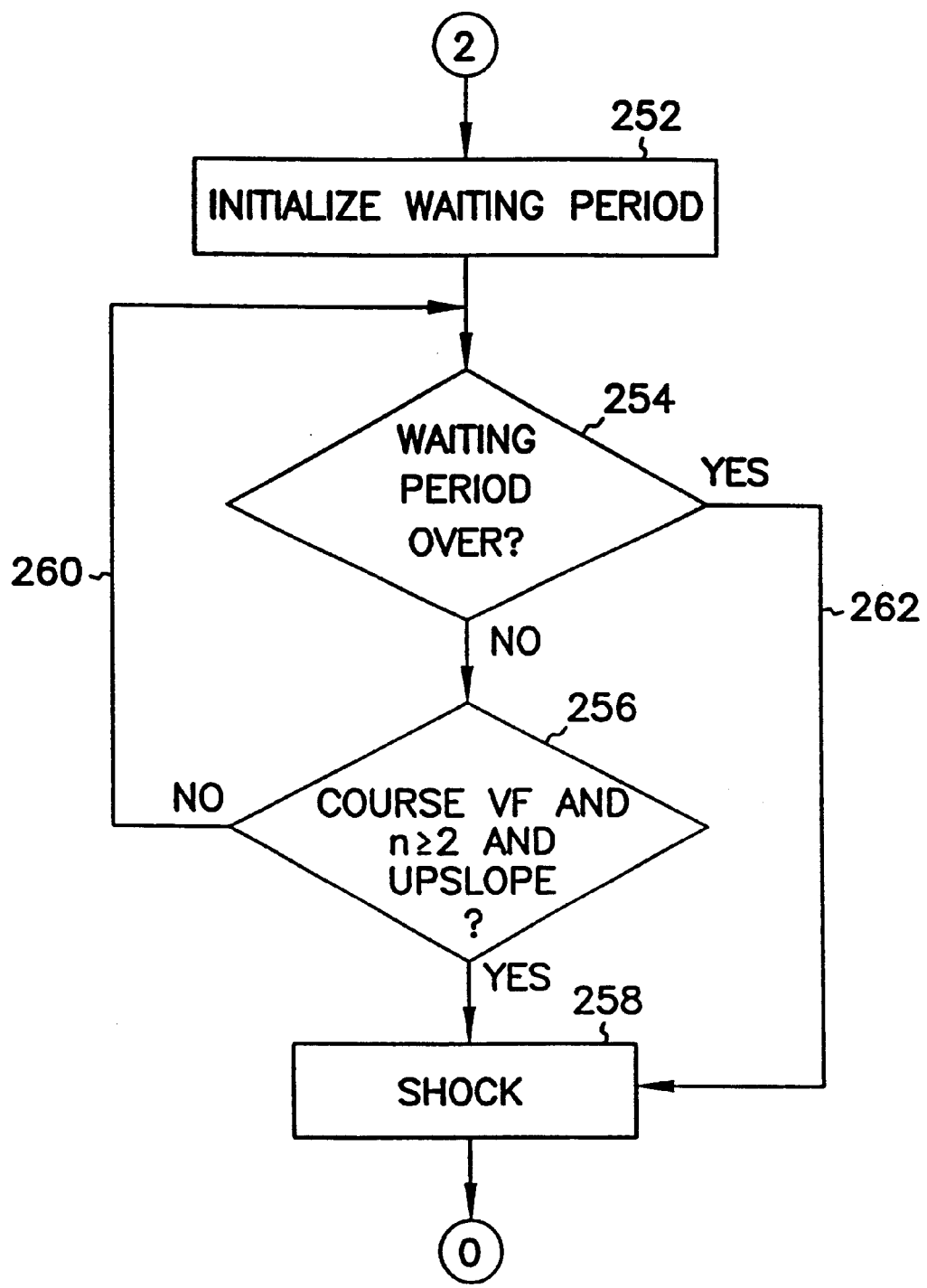
FIG. 10 is a flow chart illustrating one embodiment of the operation of the defibrillator system of FIG. 1 for delivering defibrillation shocks coordinated with ventricular fibrillation features.

Referring now to FIG. 10, there is shown an alternative embodiment of a method and operation of treating ventricular fibrillation by delivering coordinated defibrillation shocks based on monitored second cardiac signals. In one embodiment, the defibrillation shock is delivered to the heart experiencing a ventricular fibrillation during the occurrence of a waiting period timer and an up-slope portion of a coarse ventricular fibrillation complex as detected in the second cardiac region by the second cardiac signal.

The start of FIG. 10 is reached from the flow chart of FIG. 7. In the following embodiment, the sensed coarse ventricular fibrillation complex features of the second cardiac signals are taken into consideration in coordinating a defibrillation shock. At step 252, "n" (the count for a Candidate Morphology Complex discussed below) is set to zero, a waiting period is initialized, and a waiting period timer is started once a ventricular fibrillation has been detected. The waiting period timer defines the time period during which coordinated defibrillation shocks may be attempted, and after which the defibrillator system will deliver asynchronous defibrillation shocks. This time period is programmable as one of the programming parameters for the ICD 10 microprocessor 38. This time period must be kept within reasonable physiological limits, before going to asynchronous mode. In one embodiment, the waiting period timer is a programmable value within the range of 10–40 seconds, where 10 seconds is an acceptable value.

Decision block 254, which potentially is looped through multiple times, tests whether the waiting period timer programmed for coordinated defibrillation shocks has passed. If not, control passes to step 256, where the defibrillation system monitors a signal representative of ventricular electrical activity during a period of ventricular fibrillation. In one embodiment, if the defibrillation system detects in the monitored signal the occurrence of coarse ventricular fibrillation complexes, the defibrillation system then analyzes the coarse ventricular fibrillation complexes to determine an upslope, and delivers a defibrillation shock either during the upslope portion of a coarse ventricular fibrillation complex or at the expiration of the waiting period timer, where sensed conditions for the second cardiac signal is assessed to determine if a coordinated defibrillation shock is to be delivered. Therefore, at step 256 the conditions detected in the second cardiac signal must be satisfied in order for the defibrillator system to proceed to deliver a defibrillation shock to the heart at step 258.

In one embodiment, step 256 shows a list of conditions that must be detected in and satisfied for the second cardiac signal. The conditions detected in the monitored second cardiac signal include whether the second cardiac signal is a coarse ventricular fibrillation, with a coarse morphology complex value equal to or greater than a predetermined value and is on an upslope portion of the coarse ventricular fibrillation complex.

The amplitude of the morphology of the second cardiac signal detected by the second lead system 30 is taken by sense amp 60. This could be done by hardware or software in the morphology analyzer 62, part of which could also be done by software in microprocessor 38. In the present embodiment, the defibrillator system monitors the morphology signal across the first defibrillation coil electrode 34 and the second defibrillation coil electrode 36 of the second lead system 30.

In one embodiment, the defibrillator system counts the occurrences of coarse ventricular fibrillation complexes detected in the second cardiac signal, and either coordinates the delivery of the defibrillation shock with the upslope portion of a predetermined numbered occurrence of coarse ventricular fibrillation complexes or at the expiration of the waiting period timer. In one embodiment, the defibrillation shock is delivered to the heart by applying a pulse of electrical energy to the second lead system 30 and across the heart.

For the second cardiac signal, the amplitude of the current point is compared to a coarse complex threshold value. If the second cardiac signal of the current point has a peak-to-peak amplitude greater than or equal to the coarse complex threshold value, then the current point is identified as a Candidate Morphology Complex (CMC) for the second cardiac signal, and a count "n" of a second signal CMC is incremented by one. In one embodiment of the present invention, the coarse complex threshold value is 50% of the calculated SAM value.

In an additional embodiment, the value for "n" CMC is a programmable number greater than or equal to 2 and less than or equal to about 9. In the embodiment shown in FIG. 10, the "n" for the CMC is programmed to 2. At step 256, once the "n" CMC count value is equal to or above programmed number, the defibrillator system analyzes the coarse ventricular fibrillation detected in the second cardiac signal to determine if the coarse ventricular complex signal is on an upslope portion of the signal. In one embodiment, the defibrillator system test whether the current point for the second cardiac signal is on an up-slope, i.e. having a positive slope by comparing the amplitude of the current point of the second signal to the amplitude of the previous second signal point, to determine the trend.

In one embodiment, if any of the conditions for the second cardiac signal is not satisfied, control branches to path 260, to repeat the loop. If, however, these conditions are met for the second cardiac signal, control passes to step 258 where the defibrillator system proceeds to deliver a defibrillation shock. Also, if during this testing process the waiting period for the defibrillator system times out without finding the required conditions for coordinated defibrillation shocking, then once the defibrillator system loops back to 254 control passes via path 262 to step 258 where the defibrillator system proceeds to deliver an asynchronous defibrillation shock.

Figure 11:
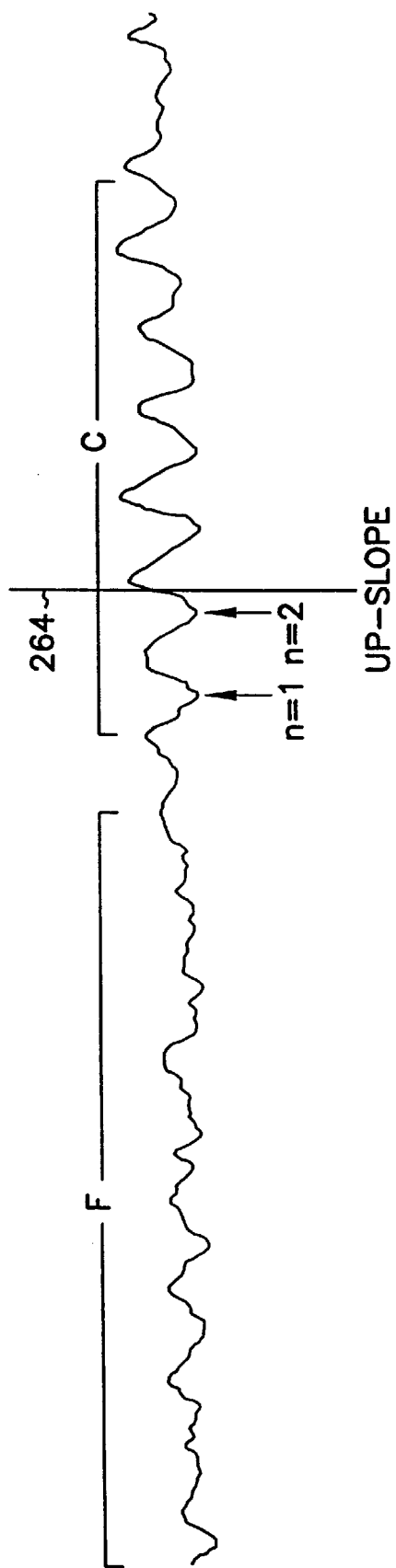
FIG. 11 is a waveform of a second signal from a heart in ventricular fibrillation, and illustrating the delivery of the defibrillation shock coordinated with ventricular fibrillation features of the second signal.

FIG. 11 shows an example of the waveforms of the defibrillator system used for delivering coordinated defibrillation shocks based on sensed coarse ventricular fibrillation complex features from the second cardiac signals. For the second cardiac signal, the zones labeled "F" are areas of fine ventricular fibrillation, and the zones labeled "C" are areas of coarse ventricular fibrillation complexes. As the ventricular fibrillation is occurring in real time, the defibrillator system is sensing and monitoring the morphology of the second cardiac signal at the second cardiac region. For the second cardiac signal, after the first major peak indicated, the defibrillator system has determined that a peak of a possible coarse ventricular fibrillation complex for the second cardiac signal has occurred, and the CMC count is incremented at the peak "n=1".

Assume, as is the case in FIG. 11, that it is in fact the start of a ventricular fibrillation complex. On the next up-slope of the second cardiac signal, as the amplitude of an up-slope signal passes the coarse complex threshold value (in the present embodiment this value is 50% of the calculated SAM value), on a first signal CMC peak count of n=2 or more the decision is made based on these criteria to deliver the defibrillation shock. The microprocessor 38 and high-energy output circuit 64 then deliver the shock shortly thereafter based on this decision. The defibrillation shock is indicated at line 264.

Following the delivery of the defibrillation shock, the sensing circuits of the ICD check to see whether the shock was successful, that is, whether the ventricular fibrillation has stopped. This is represented by a return to point "0" at the start of FIG. 2. If not successful, and if ventricular fibrillation continues, this is detected in FIG. 2, and control passes again to FIG. 10 to repeat the ventricular fibrillation therapy. The waiting period (step 254) for the second or higher passes can preferably be by-passed (or at least separately programmed from the first pass). Then if the first shock fails, the process of sensing and coordination for delivery for a second shock can begin immediately.

We claim:

1. A method of treating ventricular fibrillation, comprising the steps of:
   monitoring a first cardiac signal in a left ventricular cardiac region, where the first cardiac signal represents cardiac electrical activity;
   starting a waiting period upon detecting a ventricular fibrillation; and
   delivering a defibrillation shock within a coupling interval time period initiated upon the first cardiac signal exceeding a threshold value and during the waiting period.

2. The method of claim 1, where the predetermined threshold value is programmable in the range of 0.1 to 10 millivolts.

3. The method of claim 1, where the coupling interval time period is a programmable value in the range of 0 to 200 milliseconds.

4. The method of claim 1, where the step of monitoring further includes monitoring a second cardiac signal in a right ventricular cardiac region, and the step of delivering a defibrillation shock further includes delivering the defibrillation shock during the occurrence of both the coupling interval time period and an up-slope portion of a coarse ventricular fibrillation complex as detected in the second cardiac signal.

5. The method of claim 4, further including the step of counting coarse ventricular fibrillation complexes detected in second cardiac signal.

6. The method of claim 5, further including the step of coordinating the delivery of the defibrillation shock with the up-slope portion of an nth counted coarse ventricular fibrillation complex detected in the second cardiac signal.

7. The method of claim 6, where the nth counted coarse ventricular fibrillation complex is a number greater than or equal to 2 and less than or equal to about 9.

8. The method of claim 6, where the delivery of the defibrillation shock is further coordinated the nth coarse ventricular fibrillation complex having an amplitude greater than a coarse complex threshold value.

9. The method of claim 1, further including the step of delivering pacing level pulse of electrical energy at the left ventricular cardiac region of the heart.

10. The method of claim 1, including the step of delivering a defibrillation shock at the expiration of the waiting period timer.

11. A method of treating ventricular fibrillation, comprising the steps of:
    monitoring a first cardiac signal in a left ventricular cardiac region and a second cardiac signal in a right ventricular cardiac region, where the first cardiac signal and the second cardiac signal represent cardiac electrical activity;
    detecting up-slope portions of coarse ventricular fibrillation complexes in the first cardiac signal and the second cardiac signal; and
    delivering a defibrillation shock during an up-slope portion of a coarse ventricular fibrillation complex detected in the first cardiac signal and an up-slope portion of a coarse ventricular fibrillation complex detected in the second cardiac signal.

12. The method of claim 11, further including the step of counting coarse ventricular fibrillation complexes detected in the first cardiac signal and in the second cardiac signal.

13. The method of claim 12, further including the step of coordinating the delivery of the defibrillation shock with the up-slope portion of an nth counted coarse ventricular fibrillation complex detected in the second cardiac signal.

14. The method of claim 11, where the defibrillation shock is delivered to a heart when the amplitude of a coarse ventricular fibrillation complex detected in the first cardiac signal is greater than a coarse complex threshold value with a positive slope or rate of change and the amplitude of a coarse ventricular fibrillation complex detected in the second cardiac signal is greater than a second predetermined value with a positive slope or rate of change.

15. The method of claim 14, further including the steps of counting coarse ventricular fibrillation complexes detected in the first cardiac signal and the second cardiac signal; and coordinating the delivery of the defibrillation shock with the up-slope portion of an nth counted coarse ventricular fibrillation complex detected in the first cardiac signal and the up-slope portion of an mth counted coarse ventricular fibrillation complex detected in the second cardiac signal, where the nth and the mth counted coarse ventricular fibrillation complexes are numbers greater than or equal to 2 and less than or equal to about 9.

16. The method of claim 11, further including the step of delivering pacing level pulse of electrical energy at the left ventricular cardiac region of the heart.

17. The method of claim 11, further including the step of delivering at least one asynchronous defibrillation shock if the ventricular fibrillation is not terminated by the delivery of coordinated defibrillation shocks.

18. The method of claim 13, where the delivery of the defibrillation shock is further coordinated to the up-slope portion of an mth counted coarse ventricular fibrillation complex detected in the first cardiac signal.

19. The method of claim 18, where the delivery of the defibrillation shock is further coordinated to the mth coarse ventricular fibrillation complex having an amplitude greater than a first predetermined value.

20. The method of claim 18, where the mth counted coarse ventricular fibrillation complex is a number greater than or equal to 2 and less than or equal to about 9.

21. The method of claim 13, where the delivery of the defibrillation shock is further coordinated to the nth coarse ventricular fibrillation complex having an amplitude greater than a second predetermined value.

22. The method of claim 13, where the nth counted coarse ventricular fibrillation complex is a number greater than or equal to 2 and less than or equal to about 9.

* * * * *